United States Patent [19]

Coulter et al.

[11] Patent Number: 5,526,689
[45] Date of Patent: Jun. 18, 1996

[54] ACOUSTIC EMISSION FOR DETECTION OF CORROSION UNDER INSULATION

[75] Inventors: John E. Coulter, Lynchburg; Michael O. Robertson, Hurt; Donald M. Stevens, Lovingston, all of Va.

[73] Assignee: The Babcock & Wilcox Company, New Orleans, La.

[21] Appl. No.: 410,629

[22] Filed: Mar. 24, 1995

[51] Int. Cl.$^6$ .................................................. G01N 29/20
[52] U.S. Cl. ............................................. 73/592; 73/1 DV
[58] Field of Search .......................... 73/622, 629, 632, 73/599, 59 B, 623, 1 DV, 600, 587, 592, 646; 367/13; 364/507, 508

[56] References Cited

U.S. PATENT DOCUMENTS

| | | | |
|---|---|---|---|
| 3,824,842 | 7/1974 | Wirt | 73/599 |
| 3,946,600 | 3/1976 | Rettig et al. | 73/587 |
| 4,033,179 | 7/1977 | Romrell | 73/587 |
| 4,039,767 | 8/1977 | Leschek | 73/1 DV |
| 4,289,030 | 9/1981 | Alers et al. | 73/588 |
| 4,297,885 | 11/1981 | Hein, Jr. et al. | 73/587 |
| 4,393,711 | 7/1983 | Lapides | 73/1 DV |
| 4,406,167 | 9/1983 | Maeda | 73/622 |
| 4,619,143 | 10/1986 | Franken | 73/598 |
| 4,656,595 | 4/1987 | Hognestad | 364/507 |
| 4,685,334 | 8/1987 | Latimer | 73/599 |
| 4,732,045 | 3/1988 | Blackburn | 73/801 |
| 4,738,137 | 4/1988 | Sugg et al. | 73/587 |
| 4,758,312 | 7/1988 | Hunt et al. | 204/153.11 |
| 4,858,462 | 8/1989 | Coulter et al. | 73/40.5 A |
| 4,890,496 | 1/1990 | Birring et al. | 73/597 |
| 4,956,999 | 9/1990 | Bohannan et al. | 73/587 |
| 5,031,456 | 7/1991 | Askwith et al. | 73/587 |
| 5,065,630 | 11/1991 | Hadcock | 73/802 |
| 5,134,876 | 8/1992 | Robertson et al. | 73/40.5 A |
| 5,170,666 | 12/1992 | Larsen | 75/571 |
| 5,243,862 | 9/1993 | Latimer | 73/600 |
| 5,339,911 | 8/1994 | Whited et al. | 175/62 |
| 5,351,655 | 10/1994 | Nuspl | 122/504 |

OTHER PUBLICATIONS

Rettig, T. W. & Felsen, M. J., "Acoustic Emission Method for Monitoring Corrosion Reactions", *Corrosion–NACE*, vol. 32, No. 4, Apr. 1976. pp. 121–126.

Mansfield, F. & Stocker, P. J., "Acoustic Emission from Corroded Electrodes", *Corrosion–NACE*, vol. 35, No. 12, Dec., 1979, pp. 541–544.

*Nondestructive Testing Handbook–Second Edition*, vol. 7 (Binks, Green, Jr., and McIntire, Eds., Copyright ©1991 American Society for Nondestructive Testing, Inc.), "Ultrasonic Testing"; Section 12: Material Property Characterization—Part 2, Material Characterization Methods, pp. 386–387. vol. 5 (Miller and McIntire, Eds., Copyright ©1987 American Society for Nondestructive Testing, Inc.), Acoustic Emission Testing; Section 2: Macroscopic Origins of Acoustic Emission—Part 5, Corrosion and Stress Corrosion Cracking, pp. 58–61; Section 4: Wave Propagation—Part 4, Attenuation of Waves, pp. 103–107, no month provided.

*Primary Examiner*—Hezron E. Williams
*Assistant Examiner*—Christine K. Oda
*Attorney, Agent, or Firm*—Robert J. Edwards; Eric Marich

[57] ABSTRACT

A method and apparatus for detecting the presence of surface corrosion under insulation on a piping structure employs artificially generated, broadband acoustic sound waves to interrogate the piping structure. The sound waves are coupled into the piping structure and detected after they have propagated through and interacted with a portion of the piping structure. The amplitude of RMS voltage signals indicative of the detected sound waves is used to determine whether or not surface corrosion is present. Highly corroded pipes have been shown to yield relatively low RMS voltage signals whereas the lack of corrosion yields relatively high RMS voltage signals.

9 Claims, 4 Drawing Sheets

ACOUSTIC EMISSION FOR DETECTION OF CORROSION UNDER INSULATION

FIELD AND BACKGROUND OF THE INVENTION

The present invention relates, in general, to nondestructive examination (NDE) inspection techniques and, in particular, to a method and apparatus which uses artificially generated, broadband acoustic sound waves to interrogate an insulated piping structure and detect surface corrosion under the insulation on the piping structure.

There are enormous numbers of insulated piping systems utilized in industry, especially in the chemical and petrochemical arena. Many of these systems exist in corrosive environments where corrosion can occur unnoticed under the thermal insulation. A nondestructive examination technique for detecting surface corrosion on a piping structure is known where the inspection is performed using low frequency eddy current techniques. As described in U.S. Pat. No. 5,351,655 to Flora et al., assigned to The Babcock & Wilcox Company, assignee of the present invention, this technique does not require prior insulation removal along that portion of the piping structure being inspected. While the technique is very effective, it does require complete scanning of every pipe to ensure confidence of adequate inspection. A relatively labor-intensive effort is therefore required for thorough inspections; even to deduce the absence of corrosion. The effectiveness of the eddy current technique is also sensitive to variations in lagging types, connections, insulation moisture, etc.

Various NDE techniques are known to examine structures and detect the presence of flaws, leaks or corrosion in such structures, including what are referred to as acoustic emission (AE) techniques. The following list of patents and technical references are representative of various AE equipment and techniques known in the art.

Robertson et al. (U.S. Pat. No. 5,134,876) discloses an acoustic emission leak simulator used for non-destructive simulation of a leak in a structure.

Coulter et al. (U.S. Pat. No. 4,858,462) discloses a method and apparatus for locating a leak which produces a continuous acoustic emission having background noise and spikes. Spaced apart detectors produce signals having background noise and spikes corresponding to those of the continuous acoustic emissions and by measuring the offset between the spikes the relative position of the acoustic emission, and the relative position of the leak, can thus be determined with respect to the position of the detectors. A floating detection threshold is used and applied to the signals for eliminating background noise.

Askwith et al. (U.S. Pat. No. 5,031,456) discloses a method of detecting a void-related fault in a metal or metal alloy component. The invention is particularly useful in the detection of microbiologically-induced corrosion (MIC). Inter alia, the invention of Askwith et al. comprises filling a void-related damage with a fluid (or maintaining the component in conditions so that the void-related damage is filled with the fluid); thermally treating the component and fluid so as to produce a detectable acoustic signal; evaluating parameters conditioned to the signal; and correlating the parameters and conditions with the severity of the damage. The fluid within the MIC produced cavity or pits is thermally stimulated causing it to flow and/or boil. The acoustic energy detected during the thermal stimulation leads to the detection, location, and severity of the MIC damage.

Sugg et al. (U.S. Pat. No. 4,738,137) discloses acoustic emission non-destructive testing, in which broadband frequency noise is distinguished from narrowband acoustic emission signals, the latter being valid events indicative of structural flaws in the material being examined. This is accomplished by separating out those signals which contain frequency components both within and beyond (either above or below) the range of valid acoustic emission events.

Blackburn (U.S. Pat. No. 4,732,045) discloses a method for the rapid acoustic emission testing of pressure vessels wherein the flow rate of the pressurizing fluid is increased while maintaining the velocity of the pressurizing fluid, at an entrance of pressure vessel, below the velocity which would cause the generation of flow noise. An acoustic sensor on the pressure vessel being examined provides signals indicative of the acoustic emissions produced by the vessel during pressurization.

Rettig et al. (U.S. Pat. No. 3,946,600) discloses a method for detecting and monitoring corrosion by sensing the spontaneous propagation of elastic waves produced in materials as a result of corrosion phenomena. Certain corrosion reactions generate elastic waves which may be detected by sufficiently sensitive instrumentation to provide an identifiable acoustic signature, and correlation of these signatures with known standards provides a non-destructive inspection technique for monitoring invisible or hidden corrosion. The acoustic emission signals that are generated by corrosion reactions are characterized by a series of pulses (noise bursts) with extremely short rise times. The patent also contemplates the inclusion of controlled environments both in establishing the standard emission samples, and in making field tests, which include thermal heating via a heat lamp or electrical resistance heating to supply a controlled amount of thermal energy to the corrosion-suspect joint. The thermal energy accelerates common corrosion reactions to simplify or hasten the acquisition of the output data. Other aggressive environments may be employed to enhance or accelerate the acoustic emission process of corrosion, such as high humidity.

Leschek (U.S. Pat. No. 4,039,767) discloses a method of calibrating acoustic emission transducers, wherein random acoustic white noise is transmitted into an acoustic medium to establish a multi-mode reverberant sound field. Output responses from a standard transducer and the acoustic emission transducer to the reverberant sound field are obtained and compared to determine the sensitivity of the acoustic emission transducer.

Romrell (U.S. Pat. No. 4,033,179) discloses methods and apparatus for identifying the source location of acoustic emissions generated within an acoustic conductive medium, and which is particularly applicable to on-line monitoring of welding process to identify and locate flaws.

Hein, Jr. et at. (U.S. Pat. No. 4,297,885) discloses a method for detecting initiation and propagation of cracks in materials by adhering an acoustical emitter in the area of the material to be monitored, and then monitoring for acoustic signals emitted by the emitter.

Latimer (U.S. Pat. Nos. 4,685,334 and 5,243,862) disclose methods for ultrasonic detection and confirmation of hydrogen damage in boiler tubes. Hydrogen damage occurs on the inner surface of the boiler tubes. In the '334 patent, ultrasonic shear waves are introduced via a pitch-catch technique in the axial and circumferential directions of a boiler tube to detect the presence of hydrogen damage therein. Latimer '862 discloses a further enhancement of a hydrogen damage inspection technique which confirms that damage detected using refracted shear waves is indeed hydrogen damage, and not other inside diameter surface conditions.

Birring et al. (U.S. Pat. No. 4,890,496) discloses a method for detecting hydrogen attack by ultrasound wave velocity measurements in which ultrasound waves are transmitted on one transmitter to another along a fixed path through a steel body such as pipe. The velocity of the ultrasound wave is determined with an accuracy of one-tenth of a percent, and a decrease of a velocity by more than two percent indicates hydrogen attack. In one embodiment, either refracted longitudinal or refracted shear waves are transmitted, and the velocities thereof are determined. In another embodiment, a creeping wave is transmitted from one transducer to the other transducer with the creeping wave including a surface wave and a subsurface wave. In a third embodiment, the ultrasonic waves are transmitted into the material and the backscattered ultrasound is measured. Increases in the backscattered ultrasound are related to hydrogen attack.

Alers et al. (U.S. Pat. No. 4,289,030) discloses a nondestructive test device for detecting a flaw proximate to a welded seam in a pipe, in which a horizontally polarized shear wave is generated in a wall, and the pipe is monitored to detect a reflected horizontally polarized shear wave. Times of arrival of the generated and reflected waves are correlated to determine the circumferential position of the flaw.

Nuspl (U.S. Pat. No. 5,351,655) discloses an acoustic signal collection manifold used to monitor leaks in furnace tubes.

The *Nondestructive Testing Handbook-Second Edition*, Vol. 7 (Binks, Green Jr., and McIntire, Eds., Copyright ©1991 American Society for Nondestructive Testing, Inc.), "Ultrasonic Testing"; Section 12: Material Property Characterization - Part 2, "Material Characterization Methods", pp 386–387, discloses various material characterization methods where acoustic emission has been used to identify crucial material variables. As discussed at page 387, acoustic emission frequencies can range from the audible (sonic) to several megahertz (ultrasonic). Traditional applications of acoustic emission are disclosed, wherein passive sensors are fixed to the surface of the test object and are selected to assure sensitivity to signals generated at some distance by microdisturbances and other weak sources. The operational methods include event counts, ringdown counts, energy or amplitude distribution analysis and frequency spectrum analysis. The primary objective of traditional acoustic emission testing is the detection and location of incipient discontinuities. It can be used to monitor the presence and severity of growing cracks, plastic deformation or delaminations. It can also be used to monitor structural integrity and dynamic response and for inferring the current internal condition or state of degradation in structural components. Examples of in-process monitoring include solidification processes such as spot welding and heavy section welding.

Page 387 of this reference also includes the following paragraph:

"Another objective of acoustic emission testing is source characterization. This is hampered by signal modifications in transducers, instrumentation and especially the material. Signal modification by material microstructure, texture, diffuse discontinuity populations, mode conversions and reflections at boundary surfaces make it inherently difficult to quantitatively infer the exact nature of emitting sources. Because source characteristics are usually unknown, acoustic emission is not used for quantitative characterization of microstructure or material properties."

*Nondestructive Testing Handbook-Second Edition*, Vol. 5 (Miller and McIntire, Eds., Copyright ©1987 American Society for Nondestructive Testing, Inc.), "Acoustic Emission Testing"; Section 2: Macroscopic Origins of Acoustic Emission - Part 5, "Corrosion and Stress Corrosion Cracking", pp 58–61; Section 4: Wave Propagation - Part 4, "Attenuation of Waves", pp. 103–107 discloses that acoustic emission techniques have been used for monitoring and detecting the initiation of propagation of cracks resulting from different forms of corrosion. Further, hydrogen embrittlement itself has also been monitored with acoustic emission techniques and acoustic emission rates obtained at a value close to that of the critical stress intensity factor can be used to predict the onset of unstable crack growth. Section 4, Part 4 discloses various factors affecting the attenuation of waves, the term attenuation being used in a general sense to mean the decrease in amplitude that occurs as a wave travels through a medium. Various mechanisms have been identified that cause attenuation, and include geometric factors, dispersion effects, energy loss mechanisms, and attenuation caused by scattering and diffraction due to the media having complex boundaries and discontinuities (such as holes, slots, cavities, cracks and inclusions). Attenuation tests on actual structures have been performed which indicate that attenuation is a function of frequency (see page 106, FIGS. 14 and 15). Additionally, FIG. 17 at page 107 confirms that surface coatings applied to a structure can affect the attenuation. FIG. 17 shows the attenuation effects of foam insulation panels applied to an aluminum panel, that the attenuation that occurs is very sensitive to the technique used to apply the foam; i.e., whether it is insulation that is merely sprayed on or glued on to the surface.

A nondestructive evaluation technique to detect the presence of such corrosion without the cost inhibited task of insulation removal and replacement would be welcomed by the industry.

SUMMARY OF THE INVENTION

The present invention employs structure-coupled, artificially-generated broadband acoustic sound waves to detect the presence of and the extent of corrosion under insulation. Advantageously, the broadband acoustic sound waves are generated by and coupled to the structure via an acoustic emission leak simulator of the type disclosed in U.S. Pat. No. 5,134,876. The sound waves are allowed to propagate through and to interact with some length or portion of the pipe structure. After propagation, the sound waves are detected by piezoelectric acoustic emission (AE) sensors and converted to electrical signals for subsequent signal processing. Relatively low RMS voltage signals are indicative of highly corroded pipes, while relatively high RIMS voltage signals are indicative of pipes having little or no corrosion thereon.

The AE technique of the present invention can provide fast, preliminary, global, and less labor-intensive inspection capability for the detection of uniform-type corrosion on piping structures. It is envisioned that the technique can be employed to enhance current corrosion under insulation (CUI) inspection capabilities by providing up-front screening of corroded versus non-corroded pipes. The aforementioned low frequency eddy current technique, or other techniques, could then be utilized to inspect only those pipes displaying corrosion as determined from the present AE technique.

While it is clear that acoustic emission techniques have been used to detect the presence of flaws, or leaks, as well as corrosion in various structures, all the above-identified patents and technical references which employ traditional acoustic emission techniques refer to acoustic emissions that are, in essence, naturally produced by the structures because of the presence of flaws, leaks, or corrosion that is taking place. While Leschek teaches the application of white noise to a specimen for purposes of calibrating the sensitivity of an acoustic emission sensor, Leschek neither teaches nor suggests the use of such white noise to detect the presence of corrosion. None of the references teach or suggest the present invention's use of relatively low RMS voltage signals as indications of highly corroded pipes, in contrast to relatively high RMS voltage signals being indicative of pipes having a lack of corrosion thereon. None of the references teach or suggest applying the structure-coupled, artificially-generated, broadband acoustic sound signals to a part to be inspected so that the above-identified low or high RMS voltage signals can be detected and used as indications of whether or not corrosion is present. The closest art that might come to this teaching are perhaps the two U.S. patents to Latimer. However, Latimer discloses the use of various ultrasonic techniques to interrogate the interior surfaces of a boiler wall tube for the presence of hydrogen damage, not the exterior surface of a pipe for the presence of corrosion and while the pipe remains insulated. The '334 patent discusses at col. 1, line 49 to col. 2, line 30 the use of attenuation of the angle-beam ultrasonic shear-waves that occurs as the waves pass through the damaged area, but the ultrasonic pulses are used in the range of 2.5 MHz to 10 MHz to perform these hydrogen damage inspections. In contrast, the artificially-generated, broadband acoustic sound waves of the present invention are produced on a frequency range of approximately 0 to approximately 1 MHz.

Accordingly, one aspect of the present invention is drawn to a nondestructive inspection method for detecting the presence of surface corrosion under insulation on a piping structure. The method comprises the steps of artificially generating and coupling broadband acoustic sound waves into the piping structure; detecting the sound waves after they have propagated through and interacted with a portion of the piping structure; producing RMS voltage signals indicative of the detected sound waves; and comparing the RMS voltage signals indicative of the detected sound waves to a standard RMS voltage signal obtained from uncorroded piping to determine if surface corrosion is present on the piping structure, RMS voltage signals having an amplitude lower than the standard RMS voltage signals being representative of surface corrosion on the piping structure.

Another aspect of the present invention is drawn to a nondestructive inspection system for detecting the presence of surface corrosion under insulation on a piping structure. This system comprises: means for coupling artificially-generated, broadband acoustic sound waves into the piping structure; means for producing RMS voltage signals indicative of detected sound waves after they have propagated through and interacted with a portion of the piping structure; and means for comparing the produced RMS voltage signals with standard RMS voltage signals produced when acoustic sound waves propagates through uncorroded piping, produced RMS voltage signals having a lower amplitude than the standard RMS voltage signals being representative of surface corrosion on the piping structure.

The various features of novelty which characterize the invention are pointed out with particularity in the claims annexed to and forming a part of this disclosure. For a better understanding of the invention, its operating advantages and the specific benefits attained by its uses, reference is made to the accompanying drawings and descriptive matter in which preferred embodiments of the invention are illustrated.

DESCRIPTION OF THE PREFERRED EMBODIMENTS

The basic premise behind the present AE technique for detecting and indicating the presence of corrosion on piping structures was first indicated by the observation that significant sound wave attenuation occurred in structure-borne leak detection applications in process recovery (PR) boilers where boiler tubes displayed significant corrosion and associated insulation adhesion. At typical AE frequencies of nominally a few hundred kHz, sound waves propagating through pipes are predominantly composed of surface or plate waves. These waves are consequently "damped" by any surface coating such as paint, insulation materials, or oxide scale. Thus, the presence of uniform surface corrosion serves to "pull" energy from the propagating sound waves and increase attenuation. It should be mentioned that it has been observed that, with insulation covered piping, the insulation almost always has a tendency to adhere or bond to the pipe surface during the development of corrosion. Thus, attenuation resulting from surface corrosion is usually further magnified by the associated insulation adherence accompanying the corrosion. It is therefore theorized that the results obtained through the use of the present invention are conservative in nature.

The present invention is drawn to a non-destructive inspection technique which uses acoustic emissions to detect the presence of pipe surface corrosion, especially that which occurs under thermal insulation. The present invention can be used to detect the presence of corrosion without extensive insulation removal and replacement. The present invention is a global screening technique to identify corroded versus non-corroded pipes. The aforementioned eddy current technique, or other techniques, can then be utilized to inspect only those pipe sections displaying corrosion identified by the present invention.

The invention uses artificially-generated, broadband acoustic sound waves to interrogate pipe structures and components. The relative propagation efficiency of the sound waves is monitored, and this relative propagation efficiency is adversely affected by the amount of corrosion present on the pipe structure. The actual pipe structure does not need to be visible; it can be tested even though covered by thermal insulation.

Figure 1:
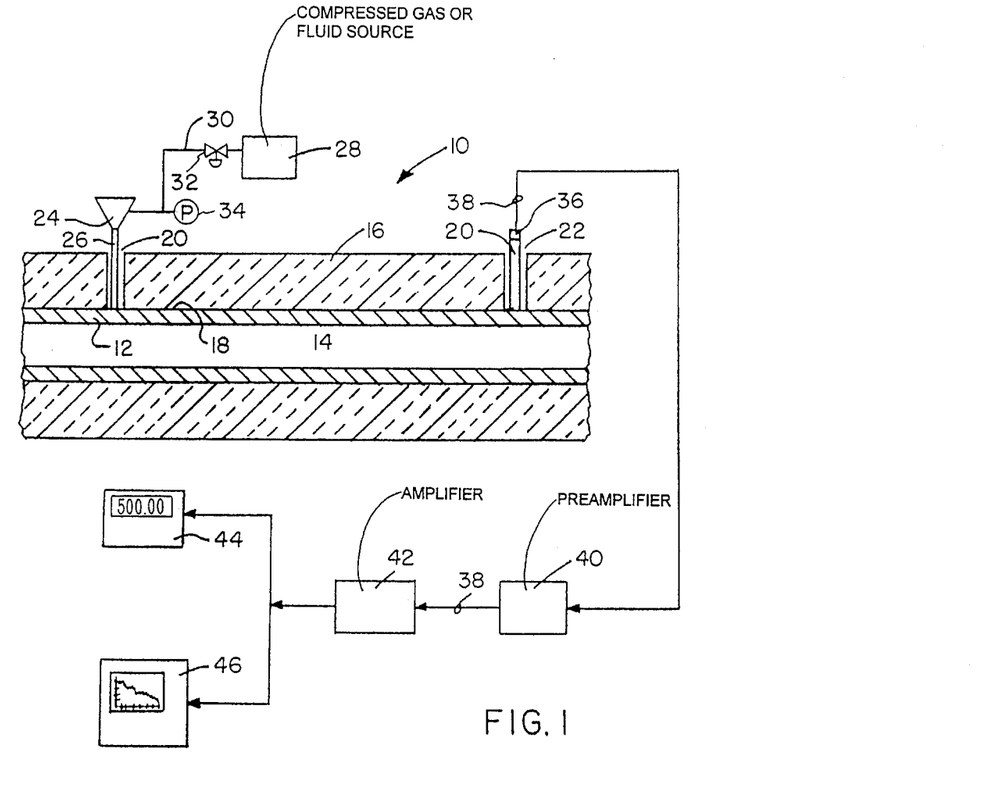
FIG. 1 is a cross-sectional view of a portion of an insulated piping structure and a schematic of the present invention as applied thereto.

Referring to the drawings generally, wherein like numerals designate the same or functionally similar elements throughout the several drawings, and to FIG. 1, in particular, there is shown a schematic representation of the present invention as applied to the task of inspecting a portion of an insulated piping structure, generally designated 10, and shown in cross-section.

The insulated piping structure 10 typically comprises a conduit or pipe 12 which conveys a material 14 therethrough. Overlying pipe 12 is a layer of thermal insulation 16. The surface corrosion of interest occurs at an interface 18 between the pipe 12 and the insulation 16. Application of the system and method of the present invention to the inspection of the insulated piping structure 10 requires gaining access to the pipe or conduit 12, but only at selected locations which will require only minimal insulation removal. To accomplish this task, access holes 20 and 22 are provided at a known, spaced distance along the piping structure 10 which defines a portion to be inspected. The access holes 20, 22 are made through the thermal insulation 16, exposing a small portion of the pipe or conduit 12 at the bottom of each access hole 20, 22.

At a first location, structure-borne, broadband acoustic sound wave (BASW) generator means 24, is acoustically coupled to the pipe 12. If necessary, due to the thickness of the insulation 16, or due to the fact that the pipe 12 is at a high temperature, acoustic sound waveguide means 26 may be employed inbetween the BASW generator means 24 and the pipe 12, to span the insulation thickness in the former case or to isolate the BASW generator means 24 from the high temperature pipe 12 in the latter case. A compressed gas or fluid source 28 is connected by means of supply line 30 to the BASW generator means 24. Valve means 32 are provided on line 30 to controllably regulate the amount of compressed gas or liquid supplied to the BASW generator means 24. Pressure measuring means 34 are provided on line 30 to indicate the pressure of the compressed gas or liquid supplied to BASW generator means 24. Advantageously, the BASW generator means 24 comprises an acoustic emission leak simulator of the type disclosed in U.S. Pat. No. 5,134,876, the text of which is hereby incorporated by reference as though fully set forth herein.

The BASW generator means 24 will artificially generate broadband acoustic sound waves which are coupled into the insulated pipe structure 10. These sound waves will propagate through and interact with a portion of the piping structure 10 being inspected. At a remote location from the BASW generator means 24, AE sensor means 36 are provided for detecting the sound waves and producing RMS voltage signals indicative of these sound waves after they have propagated through and interacted with a portion of the piping structure 10. Advantageously, the AE sensor means 36, which produces the RMS voltage signals, comprises a piezoelectric acoustic emission (ALE) sensor, provided at the bottom of access hole 22 and acoustically coupled to the pipe 12, either directly or by means of a waveguide 26 as required (due to the insulation thickness or temperature considerations as described earlier). A broadband AE sensor manufactured by Dunegan, model No. S9208 has been shown to be suitable for this purpose. Steady state sound waves produced by the BASW generator means 24 are detected by the AE sensor means 36 which produces RMS voltage signals indicative of the detected sound waves after they have propagated through and interacted with a portion of the piping structure 10. These signals are transmitted along line 38 to a preamplifier stage 40 and an amplifier stage 42 of known construction. The amplified signal at the output of amplifier stage 42 is then split and provided to a digital RMS volt meter 44 and to a spectral analyzer 46 having an oscilloscope display, also of known construction, for viewing by an operator during the inspection of the insulated piping structure 10. Surface corrosion, or the lack thereof, along the length of the insulated piping structure 10 between the BASW generator means 24 and the AE sensor means 36, will affect the intensity of the detected sound waves. The air source generates signal components at all frequencies. For the present application, one can assume, at the source, basically equal-amplitude frequencies from approximately 0 to approximately 1 MHz. Of course, with propagation, the higher frequencies are attenuated first, giving the spectra the shape shown in FIGS. 3, 4, 6 and 7. Highly corroded pipes will yield relatively low RMS voltage signals, whereas a lack of corrosion yields relatively high RMS voltage signals. Thus, by comparing the produced RMS voltage signals with standard RMS voltage signals produced when the acoustic sound waves propagate through a sample of similar but uncorroded piping, surface corrosion can be detected on the insulated piping structure 10 when the produced RMS voltage signals have a lower amplitude than the standard RMS voltage signals obtained from uncorroded piping. Existing plant piping sections of known condition can be used as a baseline to calibrate the equipment; this will minimize variations in attenuation due to non-corrosion effects.

Advantages obtained by use of the technique of the disclosure include simplicity of the technique itself, the fact that it provides quick global inspection capability for significant lengths of pipe; relative insensitivity to variations in insulation physical characteristics; only a few small access holes are required to implement the technique; the pipe material itself does not need to be conductive or ferromagnetic; and the device is easily portable.

LABORATORY TEST EXAMPLES

The laboratory test configuration utilized to prove the initial feasibility of the inventive technique was similar to that shown in FIG. 1, with the exception that the test pipe structure 12 was uninsulated. A specially-developed artificial leak simulator 24 designed according to the technique of U.S. Pat. No. 5,134,876 to Robertson et al. was employed to couple broadband acoustic sound waves into the pipe 12. Five minute epoxy was applied to the tip of the waveguide 26 to serve as a couplant between the simulator 24 and the pipe 12. A broadband AE sensor (Dunegan S9208) was coupled to the pipe 12 at a location 33 inches from the acoustic source. This particular distance was chosen to accommodate test specimen dimensions. For the tests, three pipe samples were interrogated, representing (1) a new pipe - no corrosion, (2) a pipe displaying minor surface corrosion, and (3) a pipe displaying heavy corrosion, respectively.

For the purpose of the present invention, the following objective criteria are provided as a guideline to classify piping structures having no, minimal, or heavy surface corrosion. No surface corrosion can be characterized as a surface condition wherein there is approximately a 0% reduction in through-wall thickness. Minimal surface corrosion can be characterized as a surface condition wherein there is approximately a 5% or less reduction in through-wall thickness, while heavy surface corrosion can be characterized as a through-wall thickness reduction of 20% or greater.

For each test, shop air was utilized in conjunction with the leak simulator 24 to produce and couple broadband structure-borne sound waves into the pipe 12. Steady-state sound waves were then detected with the AE sensor 36 and resulting RMS voltages and associated frequency spectra were measured. Relative signal attenuations for the three separate pipe specimens were then evaluated to prove feasibility of the technique.

Figure 2:
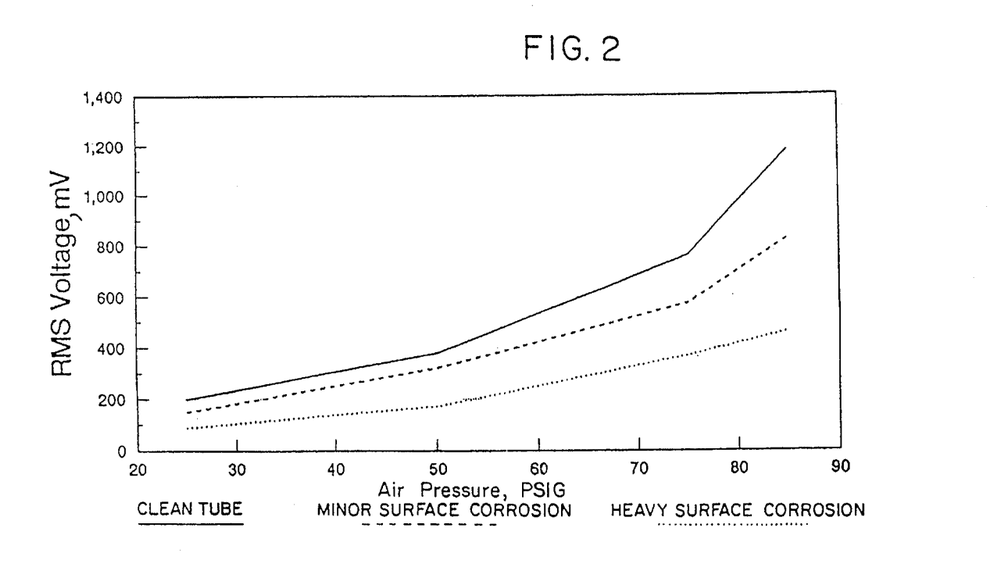
FIG. 2 is a graph showing average RMS voltage levels as a function of air pressure and degree of corrosion for various test samples used in the development of the invention.

FIG. 2 gives comparisons of RIMS voltage signal levels as derived from the unfiltered Dunegan S9208 AE sensor for the three pipe test specimens described above, as a function of air pressure at the leak simulator and the extent of pipe corrosion. Notice that the detected signal level is indirectly proportional to the amount or extent of corrosion present.

In all of the oscilloscope traces shown in FIGS. 3, 4, 6 and 7, the horizontal or X-axis, represents frequency, in Hz, while the vertical or Y-axis represents power in dBm, i.e., power in dB referenced to 1 milliwatt. For each of the FIGS. 3, 4, 6 and 7, the frequency range displayed is 0 to 250 kHz, but it will be appreciated that other frequency ranges could be employed as indicated earlier. It will be noted that the frequency spectra trace in each of the FIGS. 3, 4, 6 and 7 for the "more corroded" tube lies below the frequency spectra trace of the "lesser corroded" tube, due to the greater attenuation caused by increased corrosion.

Figure 3:
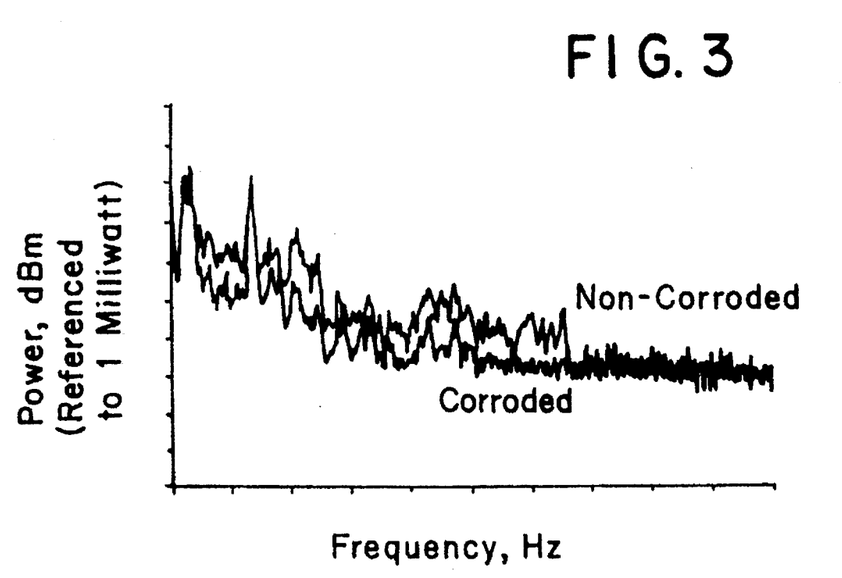
FIG. 3 is a spectral comparison of signals from non-corroded versus heavily corroded samples.

FIG. 3 gives a comparison between the frequency spectra derived from the non-corroded new tube and the heavily corroded tube.

Figure 4:
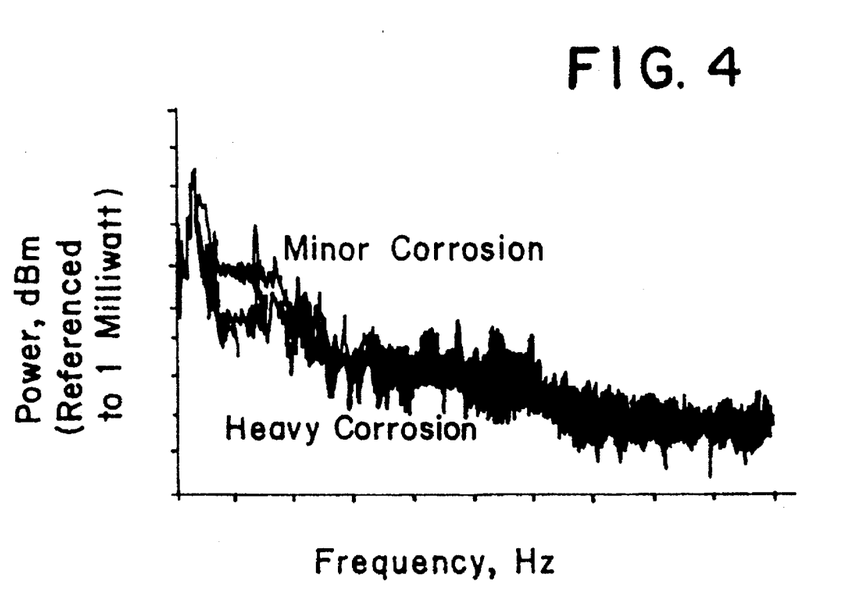
FIG. 4 is a spectral comparison of signals from the minor corroded versus heavily corroded samples.

FIG. 4 gives a comparison between the frequency spectra from the heavily corroded tube and the tube displaying only minor surface corrosion. All spectra were taken from the broadband AE sensor at the 33 inch source-to-sensor distance.

Figure 5:
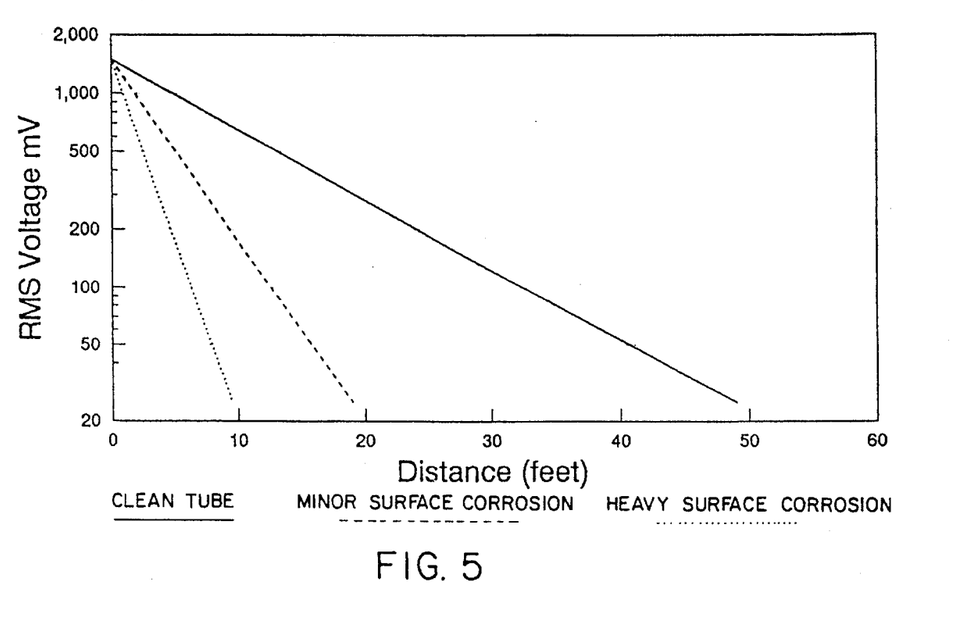
FIG. 5 is an extrapolated plot of attenuation as a function of distance for the three test samples.

FIG. 5 gives an extrapolated plot of attenuation as a function of distance for the simulated broadband sound waves as coupled to the three separate test specimens. The air pressure utilized was 85 psi. The plot was generated by taking the signal level at the simulator source (approximately 1500 mV) and at the 33 inch distance for each of the samples, then drawing a straight line through these points. The straight line was then extended down until it intersected with the average background noise for the test configuration (approximately 25 mV). The plot is shown to give a relative indication of the effects that could be expected from varying degrees of corrosion. Actual attenuation as well as feasible inspection lengths would be a function of air pressure at the simulator, operating background noises, and overall piping configurations.

Figure 6:
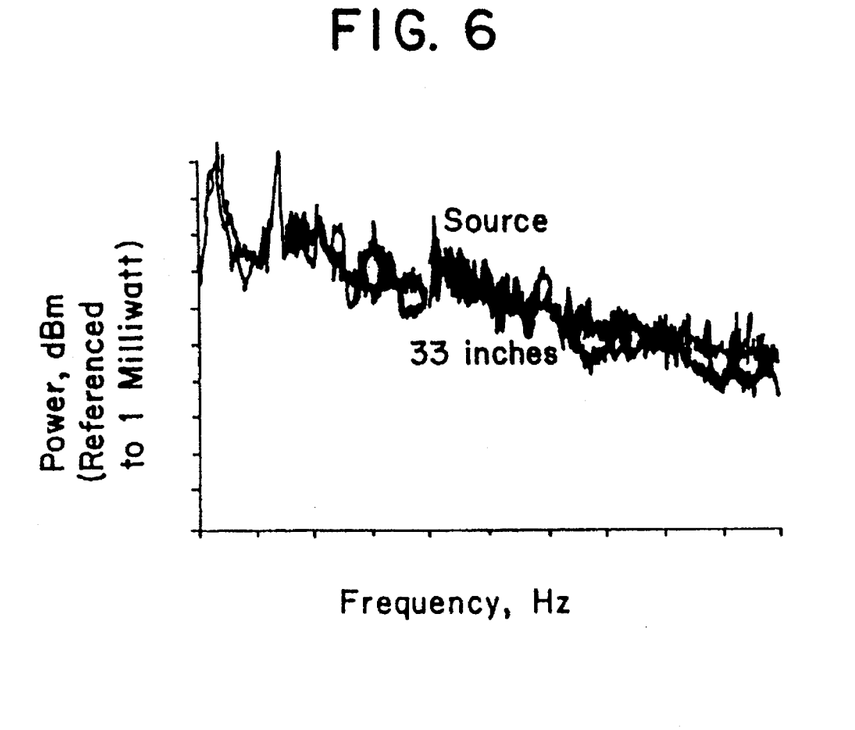
FIG. 6 is an overlay of spectra from signals derived from the non-corroded tube at the simulator source and 33 inches from the source.

FIG. 6 gives an overlay of the spectra from the non-corroded tube at the simulator source and at a distance of 33 inches from the source. Again, air pressure was 85 psi. Notice that the attenuation is not very severe.

Figure 7:
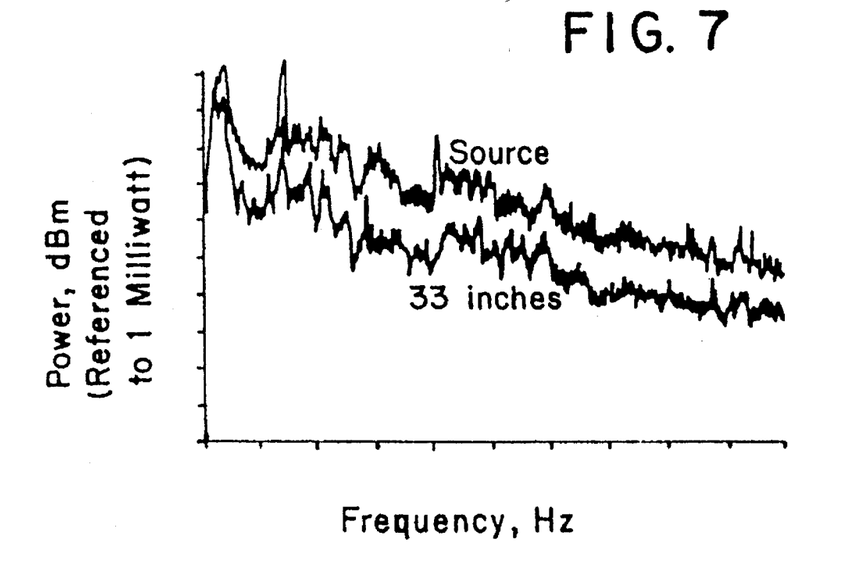
FIG. 7 is an overlay of spectra from signals derived from the heavily corroded tube at the simulator source and 33 inches from the source.

FIG. 7 gives an overlay of the spectra from the heavily corroded tube at this simulator source and at a distance of 33 inches from the source. Simulator air pressure was 85 psi. Notice that there is significant attenuation for the heavily corroded tube application.

Signal to noise (S/N) ratios between acceptable and corroded piping will vary with material type, geometries, media therein, etc. The relative differences between no corrosion and corroded (i.e., exceeding a predetermined threshold) conditions for given pipes would have to be determined, via experimentation. A baseline would need to be established to calibrate the instruments before testing is commenced. However, a rule of thumb would be that a 6 dB loss would set a minimum sensitivity of the electronics, and this would then have to be correlated with actual material losses.

The present AE inspection technique is thus useful for determining the presence of uniform corrosion on piping structures, and allows for a fast, global, and less labor-intensive inspection capability. With proper high energy sound sources, (i.e., higher air pressures) the technique should allow for inspection of sections of pipe up to 100 feet or longer, by providing higher amplitude RMS acoustic sound wave source signals. It appears that the technique is sensitive to varying degrees of uniform corrosion and could possibly be developed to predict the extent of corrosion; however, it is not clear as to whether or not the technique could be developed to be sensitive to localized corrosion. The application of the technique is intended to provide initial and global "screening" of pipe structures to determine those pipes requiring further and follow-up NDE inspections. It would be the role of these "other" NDE methods to quantify individual pipe integrity. The results obtained through use of the present invention are considered to be conservative in detecting the presence of corrosion on pipes. It is theorized that, in actual environments, substantial insulation adhesion would accompany the corrosion and would enhance overall sensitivity by producing higher attenuation of the sound waves.

While specific embodiments of the invention have been shown and described in detail to illustrate the application of the principles of the invention, those skilled in the art will appreciate that changes may be made in the form of the invention covered by the following claims without departing from such principles. Accordingly, all such changes and embodiments properly fall within the scope of the following claims.

We claim:

1. A nondestructive inspection method for detecting the presence of surface corrosion under insulation on a piping structure, comprising the steps of:

artificially generating and coupling broadband acoustic sound waves into the piping structure using an acoustic emission leak simulator;

detecting the sound waves after the sound waves have propagated through and interacted with a portion of the piping structure;

producing RMS voltage signals indicative of the detected sound waves; and comparing the RMS voltage signals indicative of the detected sound waves to a standard RMS voltage signal obtained from uncorroded piping to determine when surface corrosion is present on the piping structure, RMS voltage signals having an amplitude lower than the standard RMS voltage signal being representative of surface corrosion on the piping structure.

2. The method of claim 1, further comprising the step of using a piezoelectric acoustic emission (AE) sensor to detect the sound waves after the sound waves have propagated through and interacted with the portion of the piping structure and produce the RMS voltage signals indicative of the detected sound waves.

3. The method of claim 1, further comprising the step of using an acoustic sound waveguide to couple the acoustic emission leak simulator to the piping structure.

4. The method of claim 1, wherein the artificially-generated, broadband acoustic sound waves have a frequency in a range of approximately 0 to approximately 1 MHz.

5. A nondestructive inspection system for detecting the presence of surface corrosion under insulation on a piping structure, comprising:

acoustic emission leak simulator means for coupling artificially generated, broadband acoustic sound waves into the piping structure;

means for producing RMS voltage signals indicative of detected sound waves after the sound waves have propagated through and interacted with a portion of the piping structure; and means for comparing the produced RMS voltage signals with standard RMS voltage signals produced when acoustic sound waves propagate through uncorroded piping, produced RMS voltage signals having a lower amplitude than the standard RMS voltage signals being representative of surface corrosion on the piping structure.

6. The system of claim 5, further comprising acoustic sound waveguide means for coupling the broadband acoustic sound waves generated by the acoustic emission leak simulator means to the piping structure.

7. The system of claim 5, further comprising piezoelectric acoustic emission (AE) sensor means for producing the RMS voltage signals indicative of detected sound waves after the sound waves have propagated through and interacted with the portion of the piping structure.

8. The system of claim 5, wherein the means for comparing the produced RMS voltage signals with the standard RMS voltage signals comprise oscilloscope display means for displaying both the produced and standard RMS voltage signals for viewing by an operator.

9. The system of claim 5, wherein the artificially-generated, broadband acoustic sound waves have a frequency in a range of approximately 0 to approximately 1 MHz.

* * * * *